US00PP11379P

United States Patent [19]

Heims

[11] Patent Number: Plant 11,379

[45] Date of Patent: May 16, 2000

[54] TIARELLA PLANT NAMED 'MINT CHOCOLATE'

[75] Inventor: Dan M. Heims, Portland, Oreg.

[73] Assignee: Terra Nova Nurseries, Inc., Tigard, Oreg.

[21] Appl. No.: 09/121,022

[22] Filed: Jul. 22, 1998

[51] Int. Cl.[7] ..... A01H 5/00

[52] U.S. Cl. ..... Plt./263

[58] Field of Search ..... Plt./263

[56] References Cited

PUBLICATIONS

UPOV–ROM GTITM Computer Database Feb. 1999, GTI JOUVE Retrieval Software, Citation for 'Mint Chocolate', Mar. 1999.

The New Royal Horticultural Society Dictionary of Gardening. Huxley, Anthony, editor in chief. The Stockton Press, New York New York, 1992.

*Primary Examiner*—Howard J. Locker
*Assistant Examiner*—Wendy A Baker
*Attorney, Agent, or Firm*—Klarquist Sparkman Campbell Leigh & Whinston, LLP

[57] ABSTRACT

A new and distinct hybrid Tiarella plant characterized by deeply lobed, highly colored foliage and tawny-pink flowers in profusion.

1 Drawing Sheet

The present invention relates to a new and distinct hybrid of Tiarella, which originated as a cross-pollination of Tiarella 'Pinwheel' (unpatented, seed parent) and an unnamed, unpatented deeply lobed Tiarella seedling (pollen parent). Tiarella is in the Saxifrage family (Saxifragaceae). The new Tiarella is a result of controlled hybridization at Terra Nova Nurseries, Inc., in Canby, Oreg. This hybrid was selected from a large selection of seedlings. Seed and pollen parent plants were retained to observe habit and to compare with the new variety. The new variety has been reproduced only by asexual propagation (division and tissue culture). Each of the progeny exhibits identical characteristics to the original plant and is unlike any Tiarella offered by any American nursery or book known to me as evidenced by the following characteristics:

1. Unique form and foliage shape; and
2. Tawny-pink flowers in profusion.

Asexual propagation by division and tissue-culture as done in Canby, Oreg., shows that the foregoing characteristics and distinctions come true to form and are established and transmitted through succeeding propagations.

BRIEF DESCRIPTION OF THE DRAWING

The drawing is Tiarella 'Mint Chocolate' at the end of its blooming cycle in May.

DETAILED PLANT DESCRIPTION

The following is a detailed description of the new Tiarella hybrid based on observations of specimens in Canby, Oreg. The color descriptions are all based on The Royal Horticultural Society Colour Chart and The American Rhododendron Society publication: "A Contribution Toward Standardization of Color Names in Horticulture."

Foliage:

*Type.*—Evergreen in USDA hardiness Zones 5 and above. Herbaceous in USDA hardiness zones 3 and 4.

*Shape.*—Palmate, deeply 7-lobed, irregularly toothed; central lobe elongated, tapers to a fine point from a narrow base; lobe tip finely incised.

*Length.*—10–14 cm.

*Width.*—8–12 cm.

*Petiole length.*—Varies 10–20 cm.

*Margins.*—Crenate with a hard short point (mucronate).

*Apex.*—Rostratus (terminating gradually in a long point).

*Base.*—Cordate.

*Texture.*—Slightly rugose, light sheen.

*Leaf arrangement.*—Basal clump.

*Venation.*—Reticulate.

Flower:

*Petal count.*—5 petals. 5 calyx lobes.

*Petal shape.*—Triangular, clawed.

*Flower type.*—Complete, calyx tube campanulate, ovary superior.

*Flower size.*—0.80 cm.

*Flower number.*—40–45 blooms per raceme.

*Peduncle girth.*—1.5 mm.

*Peduncle texture.*—Puberulent.

*Blooming habit.*—Simple upright raceme to 25 cm. 30–35 racemes per second year plant. No tendency towards fasciation observed.

*Bloom period.*—Early April to Mid-May. Minor sporadic rebloom in summer and fall.

*Fragrance.*—Lightly fragrant.

Fruit:

*Type.*—Dehiscent capsule of 2 unequal parts.

*Fertility.*—Fertile.

Size:

*Height.*—19 cm (2-year-old plant grown in Canby, Oreg.).

*Width.*—30 cm (2-year-old plant grown in Canby, Oreg.).

Color Characteristics.

Foliage: Leaves have the following color: Spring/Summer upper surface: RHS 146A, Yellow-Green Group (Moderate Olive Green ARS). Central markings: RHS 200A Brown Group (Dark, grayish reddish brown ARS).

Flowers: In bud: RHS 62C, Red-Purple Group (Light Purplish-Pink ARS). In flower: RHS 155B White Group (ARS Yellowish White).

Fruit: RHS 151A Yellow Green Group (ARS Strong Greenish Yellow).

Habit: This cultivar is not stoloniferous.

Hardiness: Cold hardy to USDA Zone 3 (−40° −34° C.).

Disease: Plants grown in Canby, Oreg., show moderate susceptibility to powdery mildew. Plants are susceptibile to root rot when grown under wet conditions.

DESCRIPTION OF PARENT PLANTS

This Tiarella hybrid has characteristics that make it unique from its parents—Tiarella 'Pinwheel', which has divided and cut foliage and slight foliar markings, and the other parent, a deeply lobed Tiarella seedling with no markings. Unlike its parents, Tiarella 'Mint Chocolate' has deeply lobed, highly colored foliage and tawny-pink flowers in profusion. No other Tiarella in commerce known to me resembles Tiarella 'Mint Chocolate'.

I claim:

1. A new and distinct hybrid Tiarella plant substantially as shown and described, characterized by deeply lobed, highly colored foliage and tawny-pink flowers in profusion.

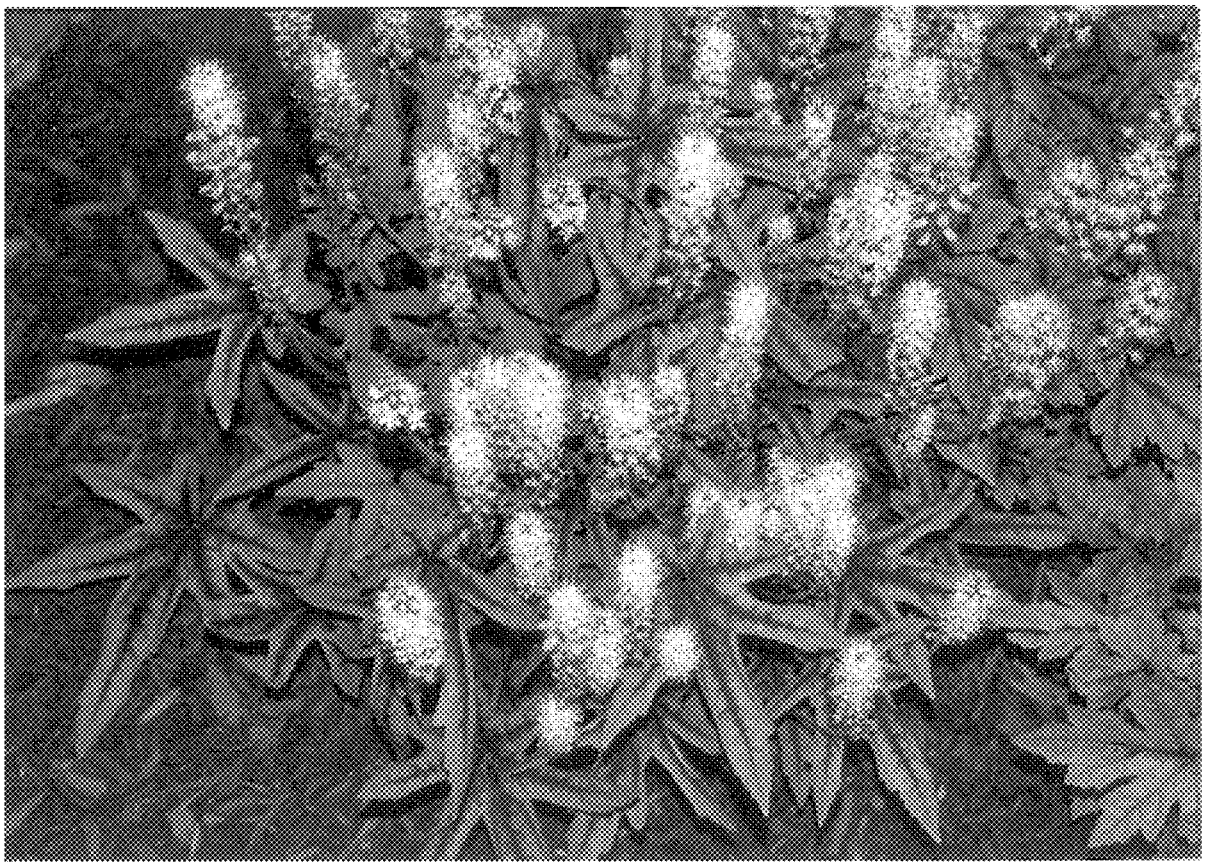

* * * * *